US012618755B2

(12) United States Patent
Adams et al.

(10) Patent No.: US 12,618,755 B2
(45) Date of Patent: May 5, 2026

(54) METHODS AND SYSTEMS FOR ASSESSING BIOELECTRIC PATTERNS

(71) Applicant: Dany S. Adam, Cambridge, MA (US)

(72) Inventors: Dany Adams, Cambridge, MA (US); Sandra Gaston, Coral Gables, FL (US)

(73) Assignee: Dany Adams, Cambridge, MA (US)

( * ) Notice: Subject to any disclaimer, the term of this patent is extended or adjusted under 35 U.S.C. 154(b) by 1003 days.

(21) Appl. No.: 17/439,768

(22) PCT Filed: Mar. 20, 2020

(86) PCT No.: PCT/US2020/023998
§ 371 (c)(1),
(2) Date: Sep. 15, 2021

(87) PCT Pub. No.: WO2020/191350
PCT Pub. Date: Sep. 24, 2020

(65) Prior Publication Data

US 2022/0099540 A1 Mar. 31, 2022

Related U.S. Application Data

(60) Provisional application No. 62/821,063, filed on Mar. 20, 2019.

(51) Int. Cl.
*G01N 1/30* (2006.01)
*C09B 57/00* (2006.01)
(Continued)

(52) U.S. Cl.
CPC ............... *G01N 1/30* (2013.01); *C09B 57/00* (2013.01); *C12N 5/0068* (2013.01);
(Continued)

(58) Field of Classification Search
CPC .... C12N 5/0068; C12N 2533/78; G01N 1/30; G01N 2001/302; G01N 2021/6439; G01N 21/6458; G01N 33/5005; C09B 57/00
See application file for complete search history.

(56) References Cited

U.S. PATENT DOCUMENTS 5,858,781 A * 1/1999 Matyas ................ G01N 1/2813
435/284.1
6,869,772 B2 3/2005 Lichtman et al.
(Continued)

FOREIGN PATENT DOCUMENTS

WO WO 2018/217266 A1 11/2018

OTHER PUBLICATIONS

International Search Report and Written Opinion for Application No. PCT/US2020/023998, mailed Jun. 12, 2020.
(Continued)

*Primary Examiner* — Kathryn Elizabeth Limbaugh
(74) *Attorney, Agent, or Firm* — Adler Pollock & Sheehan P.C.

(57) ABSTRACT

Methods and systems for assessing membrane potential are provided. In some embodiments, the methods and systems, described herein, may allow spatial patterns of membrane potential to be facilely obtained. For instance, a method may comprise transferring a population of cells from a tissue to a substrate. The transfer process may substantially maintain the viability of and/or the spatial relationship between the cells. The cells on the membrane may be exposed to a voltage sensitive dye. The dye may allow the membrane potential of individual cells on the substrate to be imaged or otherwise detected. The individual cell membrane potentials when imaged together on the substrate may form a spatial membrane potential pattern. The spatial membrane potential pattern may be used to assess one or more physiological characteristics of the cells. The methods and systems may be
(Continued)

used for a wide variety of applications, including the assessment of biopsies.

14 Claims, 5 Drawing Sheets

(51) Int. Cl.

| | |
|---|---|
| ***C12N 5/00*** | (2006.01) |
| ***G01N 21/64*** | (2006.01) |
| ***G01N 33/50*** | (2006.01) |

(52) U.S. Cl.
CPC ..... *G01N 21/6458* (2013.01); *G01N 33/5005* (2013.01); *C12N 2533/78* (2013.01); *G01N 2001/302* (2013.01)

(56) References Cited

U.S. PATENT DOCUMENTS

| | | | |
|---|---|---|---|
| 7,358,064 | B2 | 4/2008 | Klaubert et al. |
| 7,611,863 | B2 | 11/2009 | Fromherz et al. |
| 9,636,424 | B2 | 5/2017 | Pertsov et al. |
| 10,405,750 | B2 | 9/2019 | Wang et al. |
| 10,768,402 | B2 | 9/2020 | Brown |
| 2005/0181461 | A1 | 8/2005 | Zuker |
| 2008/0081990 | A1 | 4/2008 | Berenfeld et al. |
| 2012/0042398 | A1 | 2/2012 | Gottlieb et al. |
| 2014/0220681 | A1 | 8/2014 | Valamehr et al. |
| 2014/0342394 | A1 | 11/2014 | Parker et al. |
| 2016/0096036 | A1 | 4/2016 | Deisseroth et al. |
| 2017/0056041 | A1 | 3/2017 | Sabir et al. |

OTHER PUBLICATIONS

International Preliminary Report on Patentability for Application No. PCT/US2020/023998, mailed Sep. 30, 2021.

Adams et al., Endogenous voltage gradients as mediators of cell-cell communication: strategies for investigating bioelectrical signals during pattern formation. Cell Tissue Res. Apr. 2013;352(1):95-122. doi: 10.1007/s00441-012-1329-4. Epub Feb. 17, 2012.

Adams et al., Measuring resting membrane potential using the fluorescent voltage reporters DiBAC4(3) and CC2-DMPE. Cold Spring Harb Protoc. Apr. 1, 2012;2012(4):459-64. doi: 10.1101/pdb.prot067702.

Adams et al., Tissue Print V-mem Imaging: Visualizing Bioelectric Signatures in Cancer. American Association for Cancer Research Annual Meeting. Mar. 29-Apr. 3, 2019. Abstract only.

Canals et al., A Point-of-Care Device for Molecular Diagnosis Based on CMOS SPAD Detectors with Integrated Microfluidics. Sensors (Basel). Jan. 22, 2019;19(3):445. doi: 10.3390/s19030445.

Chemla, et al., "Improving Voltage-Sensitive Dye Imaging: with a Little Help from Computational Approaches", Neurophotonics, vol. 4, No. 3, 2017, p. 031215-1- 031215-12.

Chernet, et al., "Transmembrane Voltage Potential of Somatic Cells Controls Oncogene-mediated Tumorigenesis at Long-range", Oncotarget, vol. 5, No. 10, May 1, 2014, 22 pages.

Djamgoz, et al., "In Vivo Evidence for Voltage-gated Sodium Channel Expression in carcinomas and Potentiation of Metastasis", Cancers (Basel), vol. 11, No. 11, 2019, 25 pages.

Lobikin, et al., "Resting Potential, Oncogene-induced Tumorigenesis, and Metastasis: the Bioelectric Basis of Cancer in Vivo", Physical Biology, vol. 9, No. 6, 2012, pp. 1-22.

Patel, et al., "Dual Roles of Voltage-Gated Sodium Channels in Development and Cancer", International Journal of Developmental Biology, vol. 59, 2015, pp. 357-366.

Wang, et al., "Bioelectricity, Its Fundamentals, Characterization Methodology, and Applications in Nano-Bioprobing and Cancer Diagnosis", Advanced Biosystems, vol. 3, 2019, pp. 1-18.

Yang, et al., "Membrane Potential and Cancer Progression", Frontiers in Physiology, vol. 4, Article 185, Jul. 17, 2013, pp. 1-10.

* cited by examiner

METHODS AND SYSTEMS FOR ASSESSING BIOELECTRIC PATTERNS

RELATED APPLICATIONS

This application is a national stage filing under 35 U.S.C. 371 of International Patent Application Serial No. PCT/US2020/023998, filed Mar. 20, 2020, entitled "METHODS AND SYSTEMS FOR ASSESSING BIOELECTRIC PATTERNS", which claims the benefit of U.S. Application Ser. No. 62/821,063, filed Mar. 20, 2019, entitled "METHODS AND SYSTEMS FOR ASSESSING BIOELECTRIC PATTERNS," each of which is incorporated herein by reference in its entirety.

GOVERNMENT SUPPORT

This invention was made with Government support under Grant Nos. D14PC00119 (Phase I SBIR) and D15PC00054 (Phase II SBIR) awarded by the Defense Advanced Research Projects Agency. The government has certain rights in the invention.

TECHNICAL FIELD

Methods and systems for assessing membrane potential are generally described.

BACKGROUND

For many disorders, biopsy remains the gold standard for diagnosis. Typically, a biopsy contains both normal and abnormal tissue. Therefore, accurate diagnosis hinges on the ability to locate abnormal tissue within the biopsy. In many cases, the biopsy is divided into a plethora of thin sections that are evaluated by a trained professional or a complex analytical technique. The evaluation of tissue sections is often time-intensive, labor-intensive, and/or expensive. Accordingly, improved compositions and methods are needed.

SUMMARY

Methods for assessing membrane potential and related kits, systems, methods, and components associated therewith are provided. The subject matter of the present invention involves, in some cases, interrelated products, alternative solutions to a particular problem, and/or a plurality of different uses of one or more systems and/or articles.

In one set of embodiments, kits are provided. In one embodiment, a kit comprises a voltage sensitive dye and a substrate configured to bind cells.

In another set of embodiments, methods are provided. In one embodiment, a method comprises contacting a surface of a tissue with a substrate, wherein the surface of the tissue comprises cells; allowing at least a portion of the cells to bind to the substrate; and transferring the at least a portion of the cells from the surface of the tissue to the substrate, wherein a cell viability of the at least a portion of the cells after the transferring step is greater than or equal to about 75%.

In another embodiment, a method comprises exposing cells on a membrane to a voltage sensitive dye, wherein the cells are living cells.

In one set of embodiments, systems are provided. In one embodiment, a system comprises a layer on a membrane, wherein the layer comprises living cells; and a voltage sensitive dye, wherein the voltage sensitive dye is associated with at least a portion of the living cells.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Methods and systems for assessing membrane potential are provided. In some embodiments, the methods and systems described herein may allow spatial patterns of membrane potential to be facilely obtained. For instance, in some embodiments, a method may comprise transferring a population of cells (e.g., living cells) from a tissue to a substrate. The transfer process may substantially maintain the viability of and/or the spatial relationship between the cells. For example, the spatial arrangement of the cells on the membrane may correspond to the spatial arrangement of the cells in the tissue prior to the transfer process. In some embodiments, the cells on the membrane may be exposed to a voltage sensitive dye. The dye may allow the membrane potential of individual cells on the substrate to be imaged or otherwise detected. The individual cell membrane potentials when imaged together on the substrate may form a spatial membrane potential pattern. In some embodiments, the spatial membrane potential pattern may be used to assess one or more physiological characteristics of the cells and/or tissue from which the cells are derived. For instance, the spatial membrane potential pattern may be used to determine the presence and location of abnormalities (e.g., cancer) in the tissue. The methods and systems, described herein, may be used for a wide variety of applications, including the assessment of tissue biopsies and sections.

Many surgical procedures involve the removal of tissue that is sent to pathologist for assessment. Often, the pathological assessment is paramount to the diagnosis, prognosis, and/or treatment of the patient. Many traditional assessment techniques are time-consuming, labor-intensive, and/or complex. For example, tissue sectioning and histopathological analysis may take several days to complete. Moreover, many techniques utilize fixed or otherwise non-living tissue and/or cells, which limit the scope of analysis that can be performed. For example, analysis of cell proliferation cannot be performed on non-living cells. In addition, many techniques change the spatial relationship between components (e.g., cells, extracellular matrix) in the tissue sample, and therefore do not allow the location of detected abnormalities within the tissue sample and/or subject to be readily determined. Improved techniques that allow for the facile and/or expedient assessment of a broad range of physiological features are needed.

The present disclosure relates to the surprising discovery that certain substrates and voltage sensitive dyes can be used to accurately analyze cells (e.g., living cells) and map physiological features to specific tissue locations in a facile, expedient, and/or cost-effective manner. In general, the methods and systems, described do not suffer from one or more limitations of traditional assessment techniques.

Figure 1A:
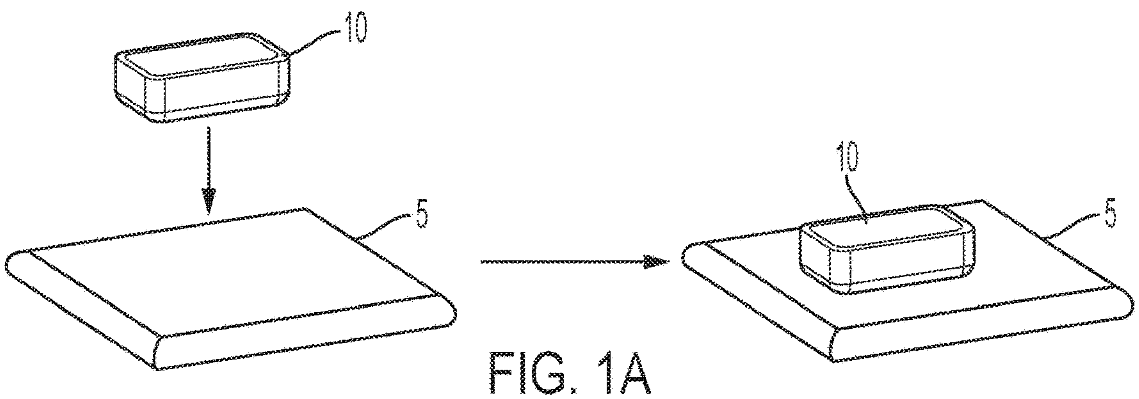
FIGS. 1A-D show a schematic of a method, according to one set of embodiments.

As described herein, a substrate and a voltage sensitive dye may be used to assess one or more characteristics of cells (e.g., living cells). In some embodiments, the cell may be from a tissue (e.g., biopsy, specimen, living tissue). For instance, as illustrated in FIG. 1A, substrate 5 may be brought into contact with the surface of tissue 10. In some instances, at least a portion (e.g., substantially all) of the cells and/or extracellular matrix present on the surface of the tissue may form a relatively strong association (e.g., non-covalent bond, covalent bond) with the substrate. In some such cases, the substrate may be configured to form strong associations with cells and/or biological molecules (e.g., extracellular matrix molecules). The substrate (e.g., nitrocellulose) and the tissue may be allowed to remain in contact for a sufficient period of time to allow for associations (e.g., non-covalent bonds, covalent bonds) to form between the substrate and material (e.g., cells, extracellular matrix) on the surface of the tissue. For example, substrate 5 and tissue 10 may remain in contact for greater than or equal to about 1 second and less than or equal to about 60 seconds (e.g., greater than or equal to about 1 second and less than or equal to about 30 seconds). In other embodiments, the cells may be derived from a culture of cells.

After a suitable amount of time, the tissue may be removed from the substrate or vice versa. In some embodiments, at least a portion of the material (e.g., cells, extracellular matrix) on the surface of the tissue may be transferred to the substrate upon removal. For example, abnormal material (e.g., cancer cells) and/or normal material (e.g., cells, extracellular matrix) from the surface of the tissue may be transferred to the substrate. In certain embodiments, a relatively large percentage of the material on the surface of the tissue that was in contact with the substrate may be transferred to the substrate. For instance, in some embodiments, material from greater than or equal to about 50% (e.g., greater than or equal to about 60%, greater than or equal to about 75%, greater than or equal to about 90%) of the tissue area in contact with the substrate may be transferred to the substrate. In some such cases, greater than or equal to about 50% (e.g., greater than or equal to about 60%, greater than or equal to about 70%, greater than or equal to about 80%, greater than or equal to about 90%) of the cells on the surface of the tissue are transferred to the substrate.

In some embodiments, the transferred material may have substantially the same shape and/or spatial relationship between tissue components (e.g., cells, extracellular matrix) as the tissue prior to the transfer. For instance, the transferred material on the substrate may form a shape having a perimeter. The perimeter of the shape of the transferred material may be substantially the same as the perimeter of the surface of the tissue. For example, the perimeter of the transferred material (e.g., layer on material) on the substrate may be within about 30% (e.g., about 20%, about 15%, about 10%, about 5%, about 2%) of the perimeter of the surface of the tissue. As another example, the area of the transferred material (e.g., layer on material) on the substrate may be within about 30% (e.g., about 20%, about 15%, about 10%, about 5%, about 2%) of the area of the surface of the tissue. In certain embodiments, the arrangement of the material remaining on the substrate may be at least a partial mirror image of the surface of the tissue. The arrangement of material on the substrate may be at least a partial mirror image of the surface of the tissue prior to the contacting step. That is, the spatial arrangement of the material on the membrane may correspond to the spatial arrangement of the material (e.g., cells, extracellular matrix) on the surface of the tissue prior to the contacting step. In some such cases, the distance (e.g., center-to-center distance) between any given cell and another cell on the substrate may be substantially the same as the pre-transfer distance (e.g., center-to-center distance) between any given cell and another cell on the surface of the tissue. For example, the distance between any given cell and another cell may be within about 30% (e.g., about 20%, about 15%, about 10%, about 5%, about 2%) of the pre-transfer distance on the surface of the tissue.

In some embodiments, the viability and/or integrity of the material may be substantially maintained during transfer. For instance, living cells on the tissue surface may be transferred to the substrate with little or no reduction in cell viability (e.g., less than or equal to about 10% reduction in cell viability). In such cases, a layer of material including living cells is present on the surface of the substrate. In some embodiments, the material on the substrate may have at least some (e.g., substantially all) of the physiological features (e.g., pathophysiological features) present on the surface of the tissue prior to the contacting step. For example, living cells and other material (e.g., extracellular matrix) may be transferred to the substrate with minimal or no adverse effects on one or more features (e.g., phenotype, genotype, structural conformation) important for a given analysis. For instance, abnormal cells transferred to the substrate may substantially maintain their abnormal characteristics. Conversely, normal cells transferred to the substrate may substantially maintain their normal characteristics. In some embodiments, the relatively high fidelity of the transfer process with respect to spatial arrangement and physiological features may allow the tissue location of specific physiological features (e.g., abnormal cells) to be readily determined, as described in more detail below.

Figure 1B:
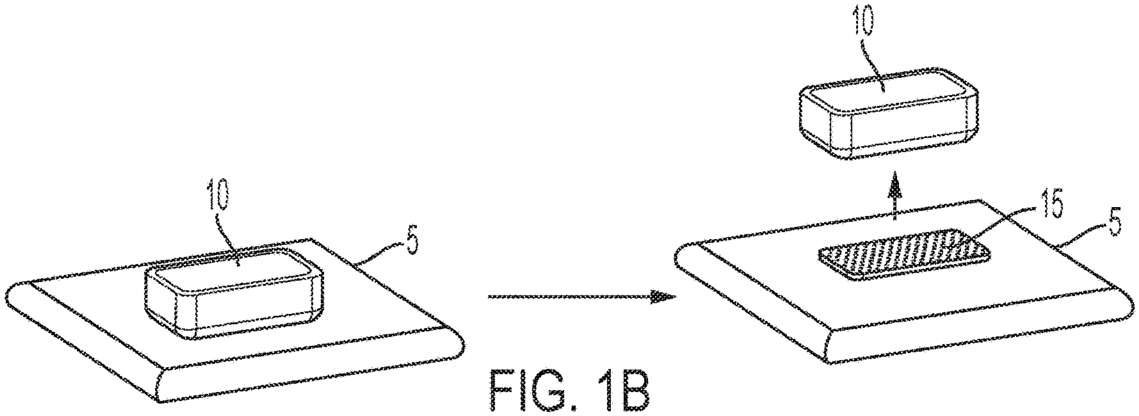

A non-limiting example of the transfer process is shown in FIG. 1B. As illustrated in FIG. 1B, after a suitable period of time, tissue 10 may be removed from substrate 5. At least a portion of the material on the surface of the tissue may be transferred to substrate 5 to form layer 15. In some embodiments, layer 15 may comprise cells and/or extracellular matrix from tissue. As illustrated in FIG. 1B, layer 15 may be a mirror image of the surface of tissue 5 prior to the contacting step. In some such cases, layer 15 may be relatively continuous. In certain cases, layer 15 may be a partial mirror image of the surface of tissue 5 prior to the contacting step. In some such cases, layer 15 may be a discontinuous layer. In generally, layer 15 may be relatively thin (e.g., less than or equal to about 50 microns). For example, layer 15 may comprise a single monolayer of cells that correspond to the outermost monolayer of cells on the surface of the tissue prior to the contacting step. As another example, layer 15 may comprise multiple layers of cells extracted from positions at or near the surface of the tissue during the removal process. Regardless of the number of cell layers, the thickness of layer 15 may be less than the penetration depth of electromagnetic radiation (e.g., visible wavelengths) for a given technique (e.g., microscopy). For instance, the thickness of the layer may be less than or equal to about 1 mm, less than or equal to about 500 microns, less than or equal to about 250 microns, less than or equal to about 100 microns, less than or equal to about 75 microns, less than or equal to about 50 microns, less than or equal to about 40 microns, less than or equal to about 30 microns, less than or equal to about 20 microns, or less than or equal to about 10 microns.

Figure 1C:
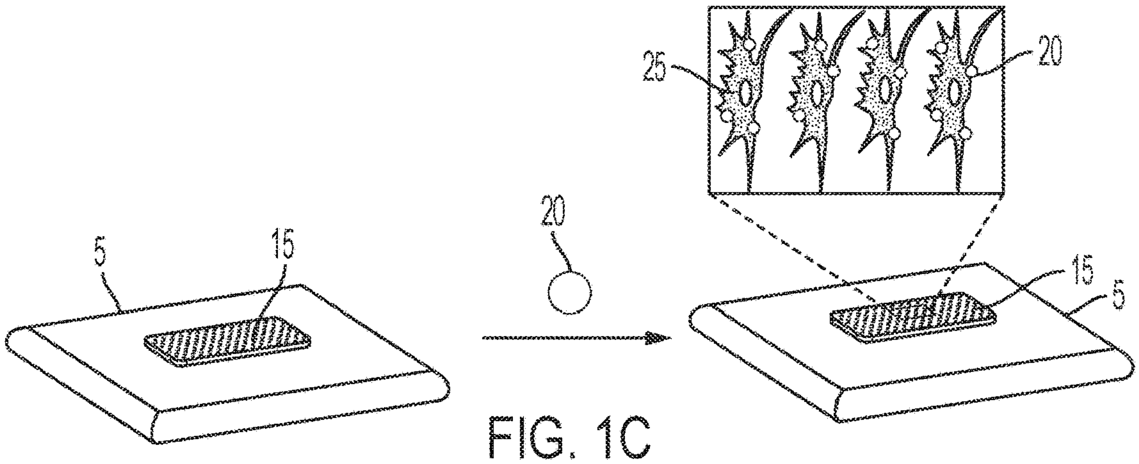

In some embodiments, layer 15 may be subjected to one or more analyses. In certain embodiments, the one or more analyses are conducted under conditions that allow one or more features of layer 15 that are important for a given analysis to be maintained. For instance, in embodiments in which the transferred material (e.g., layer 15) comprises living cells, the analysis(es) may be conducted under conditions that substantially maintain cellular viability and function. For example, the living cells on the substrate may undergo one or more processes characteristic of living cells (e.g., cellular respiration, cellular division, cell cycle change) prior to, during, and/or after the analysis(es). In some embodiments, the membrane potential of layer 15 may be assessed. For instance, as illustrated in FIG. 1C, layer 15 may be exposed to a voltage sensitive dye 20. The voltage sensitive dye may associate with the cell membranes of cells 25 as shown in the inset of FIG. 1C. In some embodiments, cells 25 may be living cells.

In certain embodiments, the tissue and/or cells may be exposed to one or more reagents (e.g., voltage sensitive dye) for an analysis prior to contact with the substrate and/or transfer of cells to the substrate. For instance, a plant sample may be exposed to a voltage sensitive dye prior to the contact with the substrate. Regardless of whether the cells are exposed to a reagent, such as a dye, prior to or after transfer of the cells to the substrate, one or more analyses may be performed on layer 15.

In some embodiments, voltage sensitive dye 20 may allow the resting potential of at least a portion (e.g., greater than or equal to about 70%, greater than or equal to about 90%, substantially all) of the living cells in the layer to be assessed (e.g., imaged). In certain embodiments, voltage sensitive dye 20 may allow the action potential of at least a portion (e.g., greater than or equal to about 70%, greater than or equal to about 90%, substantially all) of the living cells in the layer to be assessed (e.g., imaged). Regardless of whether the resting or action potential is assessed, in some embodiments, the individual cell potentials (e.g., membrane potentials) may be assessed together on the substrate to produce a spatial membrane potential pattern. For instance, as illustrated in FIG. 1D, a device configured to detect electromagnetic radiation (e.g., fluorescence microscope) may be used to analyze individual cells and/or layer 15 as a whole.

In some embodiments, the device may be configured to detect one or more properties of electromagnetic radiation (e.g., visible light). For instance, the device may be configured to detect the absorbance wavelength, emission wavelength, intensity, and/or duration of electromagnetic radiation for individual cells and/or layer 15 as a whole. In some instances, the device may produce an image of the substrate that contains information regarding one or more properties of electromagnetic radiation (e.g., visible light) for individual cells and/or layer 15 as a whole. For instance, the image may contain information regarding the absolute value, variance in value, and/or pattern of values for one or more properties (e.g., emission wavelength, intensity) for individual cells and/or layer 15 as a whole. In certain embodiments, the pattern of one or more properties of electromagnetic radiation (e.g., intensity) across the substrate may form the spatial membrane potential pattern. In some embodiments, the information contained within the image and/or the image itself may allow certain physiological features of the cells and/or layer to be determined.

Figure 1D:
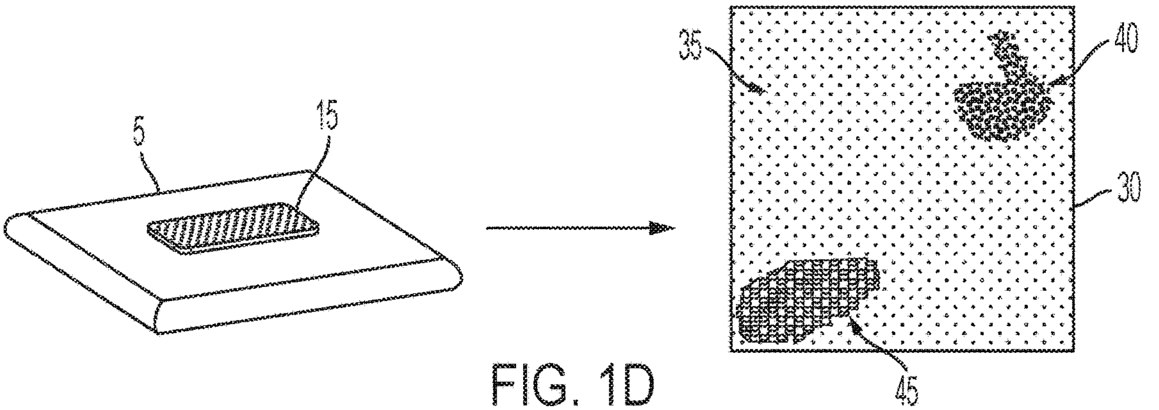

For instance, as illustrated in FIG. 1D, the device may produce a multi-dimensional (e.g., two- or three-dimensional) image 30 of the substrate. The image may contain information regarding one or more electromagnetic properties (e.g., intensity, wavelength) of the individual cell and/or layer 15. In certain embodiments, the image may show or otherwise contain information regarding the spatial membrane potential pattern formed by the cells in layer 15. For instance, image 30 may be a fluorescence image (e.g., two- or three-dimensional image) that visually depicts the spatial membrane potential pattern of individual cells and/or the layer as a whole. In some such cases, the visual depiction may be based on the variance in fluorescence intensity and/or emission wavelength across the substrate. Image 30 may allow certain physiological features of the cells and/or layer to be determined. In some embodiments, cells with different physiological features may have one or more different electromagnetic properties (e.g., intensity, emission wavelength, variation in intensity or wavelength). For instance, as illustrated in FIG. 1D, cells and/or regions containing normal cells (e.g., region 35) may have a different membrane potential pattern than cells and/or regions containing abnormal cells (e.g., region 40, region 45). In some embodiments, the image 30 may allow different types of abnormalities to be distinguished and/or identified. For example, as shown in FIG. 1D, abnormal region 40 has a different membrane potential pattern than abnormal region 45.

In some embodiments, image 30 may be compared to one or more control images. In some instances, a control image may comprise normal cells. In certain cases, a control image may comprise abnormal cells. Differences between the control image and image 30 may be used to identify certain physiological features present in layer 15. In some embodiments, the device may transmit the image or derivative thereof to a computer for assessment of image 30. The computer may use an algorithm to determine one or more physiological features present in layer 15. In certain embodiments, image 30 may be analyzed by a trained professional.

In general, the methods, described herein, may be used for a wide variety of applications. For instance, the methods may be used to determine the presence, absence, and/or extent (e.g., grade) of a pathological disorder in a tissue sample (e.g., tissue biopsy, surgical specimen, core biopsy) and/or subject. In some embodiments, the pathological disorder is cancer. In some such cases, the methods may be used to determine the presence, absence, and/or grade of cancer in a tissue sample (e.g., tissue biopsy, surgical specimen) and/or subject. Non-limiting examples of cancers that may be determined and/or classified using the methods described herein include oral cancer, cardiac cancer, lung cancer, gastrointestinal cancer, genitourinary tract cancer, liver cancer, bone cancer, nervous system cancer, gynecological cancer, skin cancer, thyroid gland cancer, or adrenal gland cancer. In some instances, the cancer is breast cancer or prostate cancer.

In some embodiments, the methods may be used to evaluate the response of living cells to a stimuli (e.g., chemical, physical). For instance, referring to FIG. 1D, the resting membrane potential pattern of layer 15 may be imaged before and after application of a stimulus, such as a chemical compound (e.g., pharmaceutically active agent). The before and after images may be compared to ascertain changes in one or more physiological features due to the stimulus. In some embodiments, the methods may be used to evaluate the change in one or more properties (e.g., division rate) over time. In some such cases, images of the living cells on the substrate may be taken at certain time intervals and compared with each other and/or control images to ascertain changes in one or more physiological features.

In some embodiments, a method may utilize a voltage sensitive dye. In general, any suitable voltage sensitive dye may be used. Non-limiting examples of suitable dyes may be found in International Patent Application Publication No. WO2018/217266 (International Patent Application No. PCT/US2018/020621), filed Nov. 29, 2018, entitled "Voltage Sensitive Dyes," by Bardon et al., which is incorporated by reference in its entirety. In some embodiments, the voltage sensitive dye comprises one or more charged groups (e.g., two charged groups). In some instances, the voltage sensitive dye may comprise positively charged groups. In certain cases, the voltage sensitive dye may comprise negatively charged groups. Without wishing to be bound by theory, in some aspects, the one or more charged groups may serve as an anchor, such that the one or more charged groups are outside the cell membrane while the remaining portion of the voltage sensitive dye is inside the cell membrane.

In some embodiments, the voltage sensitive dye is:

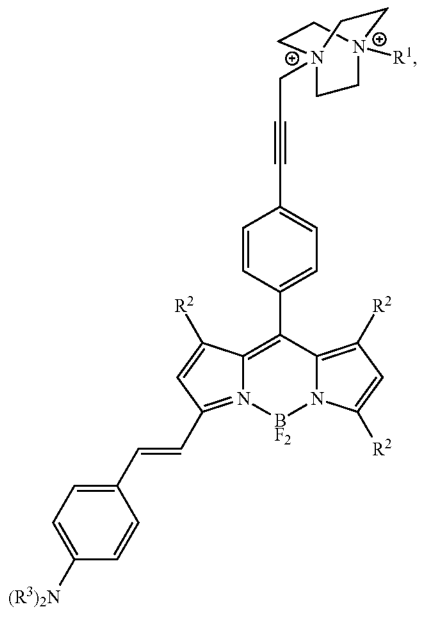

-continued

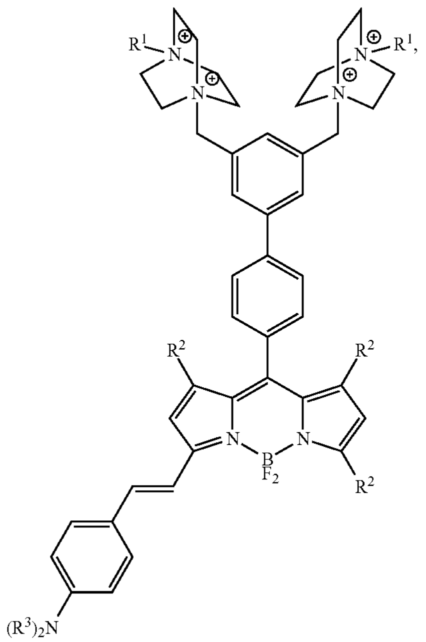

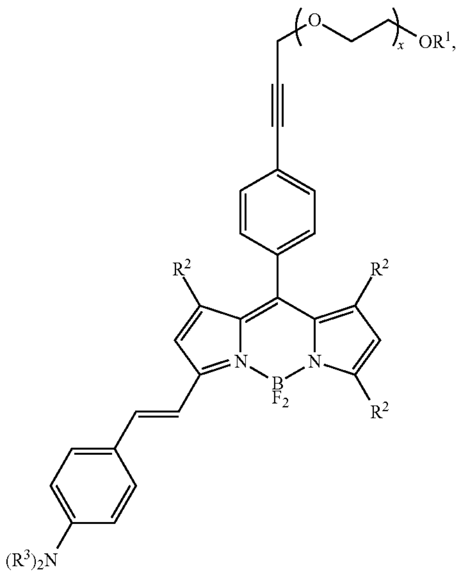

-continued
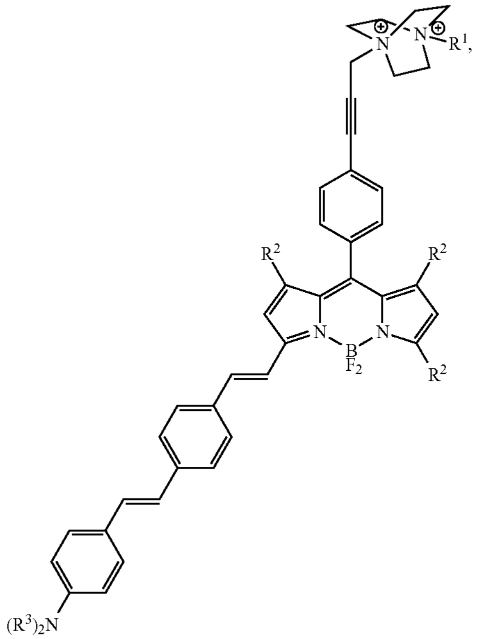
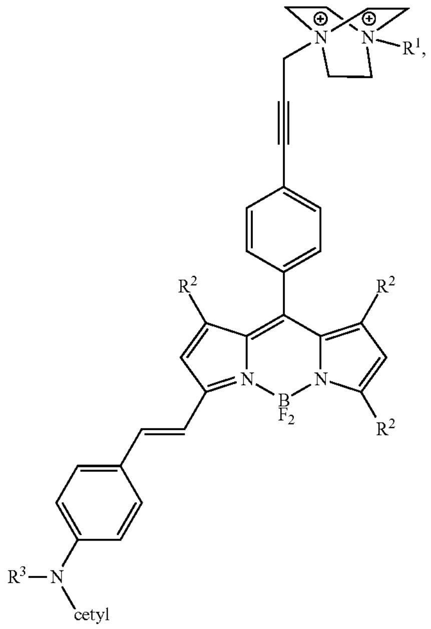
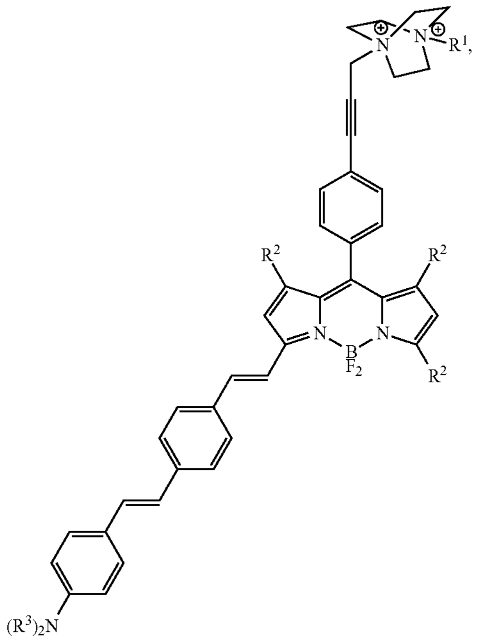
-continued
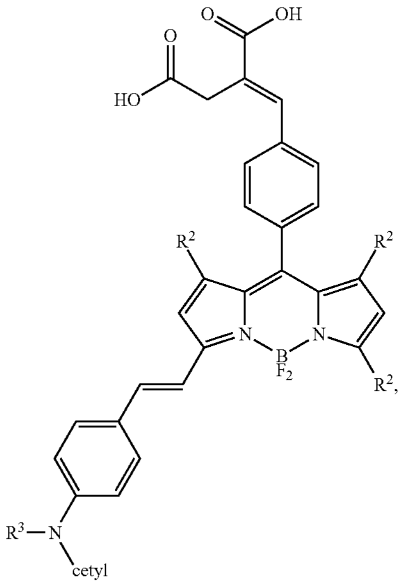

-continued

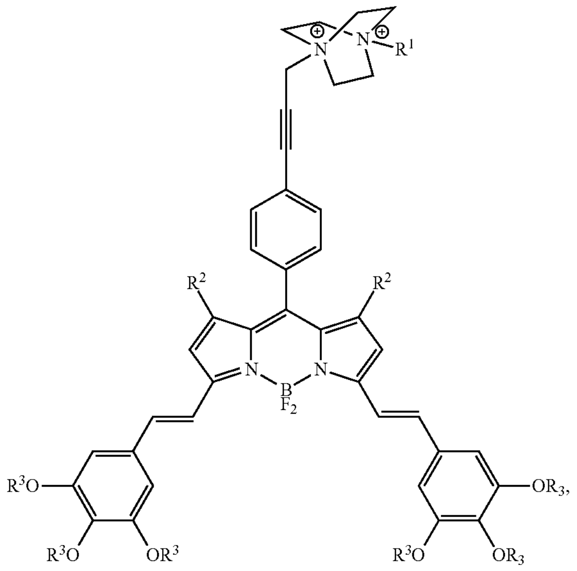

-continued

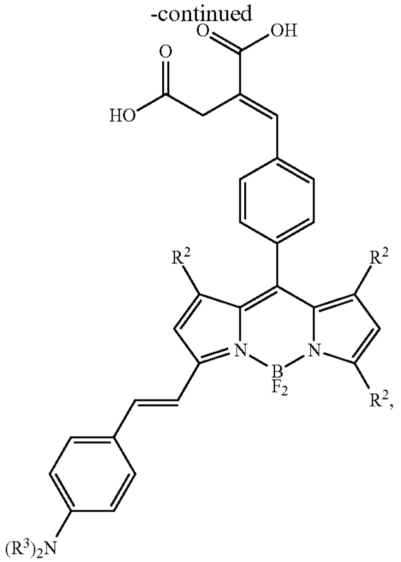

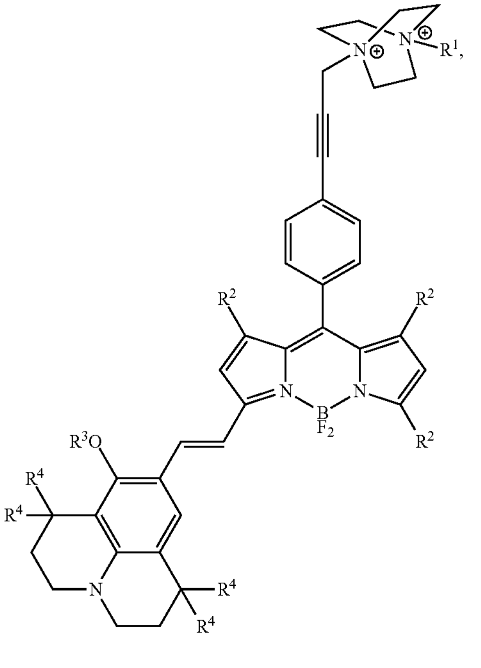

or a salt thereof, wherein:

each $R^1$ is independently —$C_1$-$C_6$ alkyl, —$C_2$-$C_6$ alkenyl, —$C_3$-$C_6$ alkynyl, or H;

each $R^2$ is independently —$C_1$-$C_6$ alkyl, —$C_2$-$C_6$ alkenyl, —$C_3$-$C_6$ alkynyl, or H;

each $R^3$ is independently —$C_1$-$C_6$ alkyl, —$C_2$-$C_6$ alkenyl, —$C_3$-$C_6$ alkynyl, or H;

each $R^4$ is independently —$C_1$-$C_6$ alkyl, —$C_2$-$C_6$ alkenyl, —$C_3$-$C_6$ alkynyl, or H;

each hydrogen atom in —$C_1$-$C_6$ alkyl, —$C_2$-$C_6$ alkenyl, or —$C_3$-$C_6$ alkynyl is independently optionally substituted with deuterium, halogen, —OH, —CN, —$OR^1$, —$CO_2H$, —$C(O)OR^1$, —$C(O)NH_2$, —$C(O)NH(C_1$-$C_6$ alkyl), —$C(O)N(C_1$-$C_6$ alkyl$)_2$, —$SC_1$-$C_6$ alkyl, —$S(O)C_1$-$C_6$ alkyl, —$S(O)_2C_1$-$C_6$ alkyl, —$S(O)NH$ ($C_1$-$C_6$ alkyl), —$S(O)_2NH(C_1$-$C_6$ alkyl), —$S(O)N(C_1$-$C_6$ alkyl$)_2$, —$S(O)_2N(C_1$-$C_6$ alkyl$)_2$, —$NH_2$, —$NH(C_1$-$C_6$ alkyl), —$N(C_1$-$C_6$ alkyl$)_2$;

each $R^1$ is independently deuterium, —$C_1$-$C_6$ alkyl, —$C_2$-$C_6$ alkenyl, —$C_2$-$C_6$ alkynyl, —$C_3$-$C_6$ cycloalkyl, or —$C_1$-$C_6$ alkyl-O—$C_1$-$C_6$ alkyl; and x is between 1 and 14.

In certain embodiments, the voltage sensitive dye is:
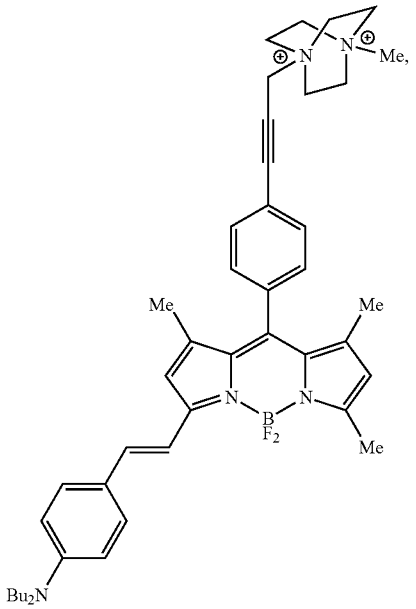
-continued
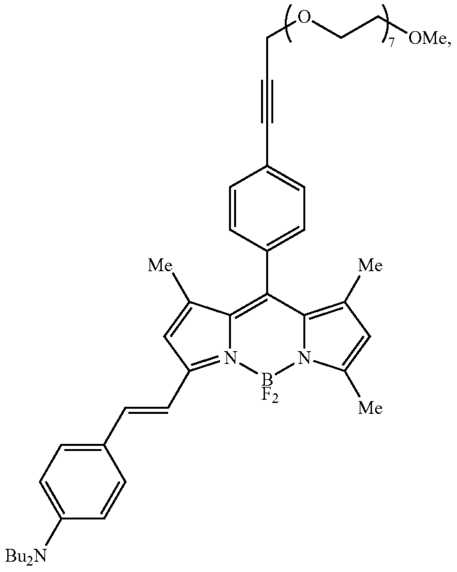
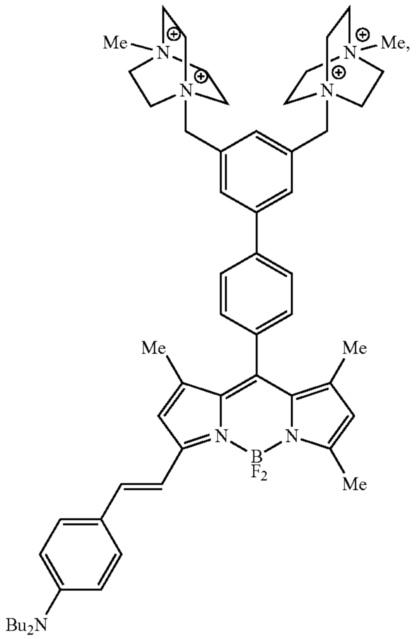
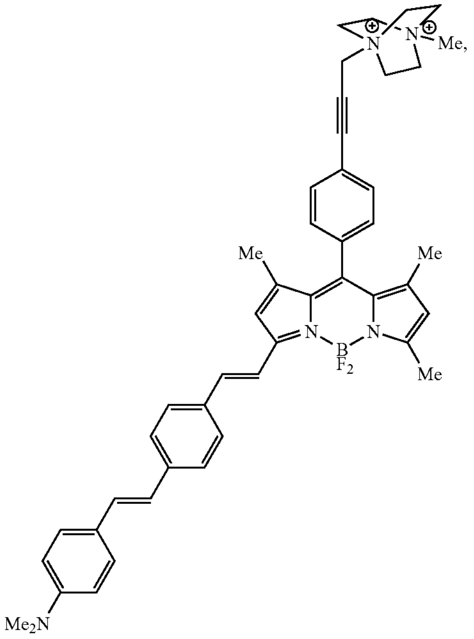

-continued
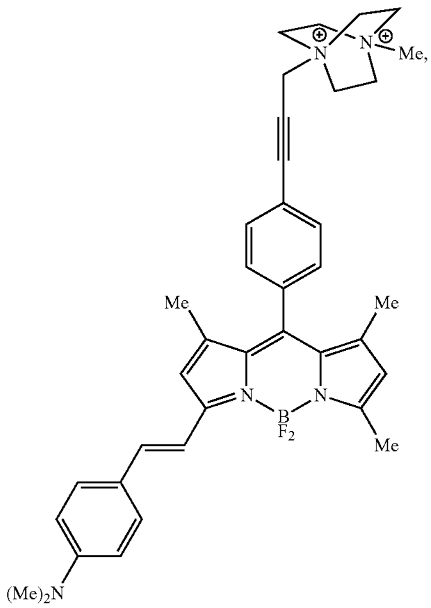
-continued
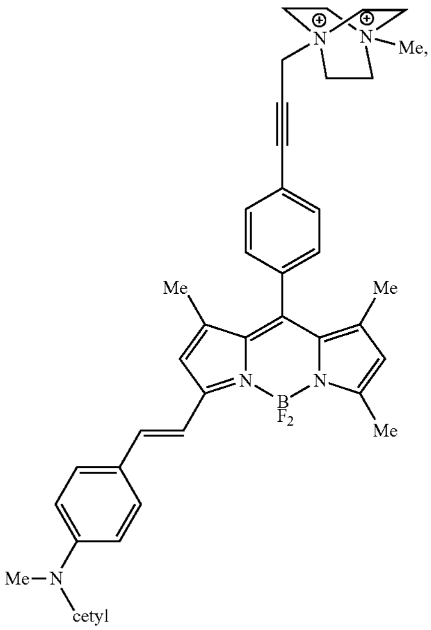
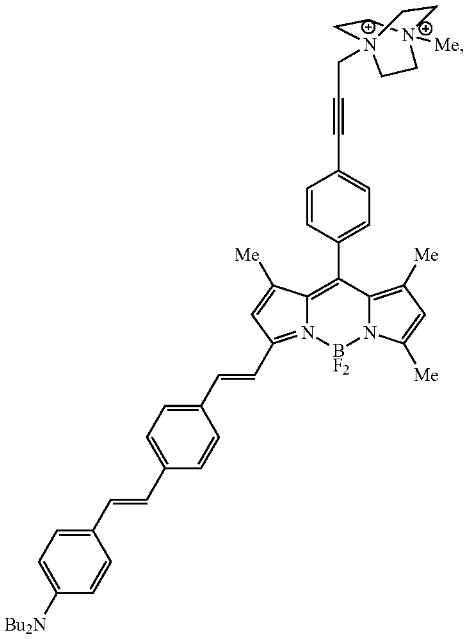
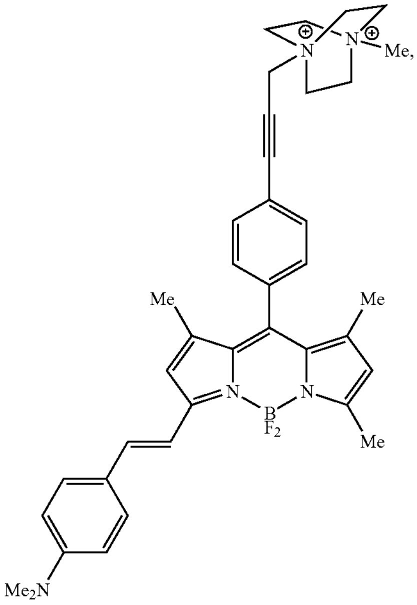

-continued
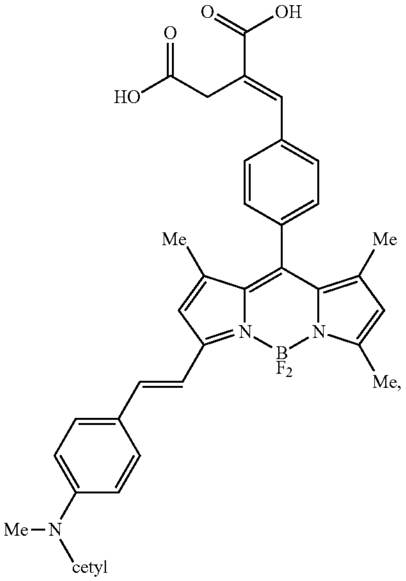
-continued
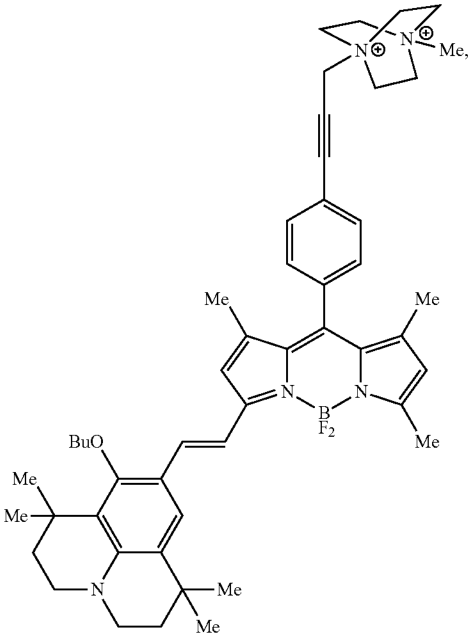
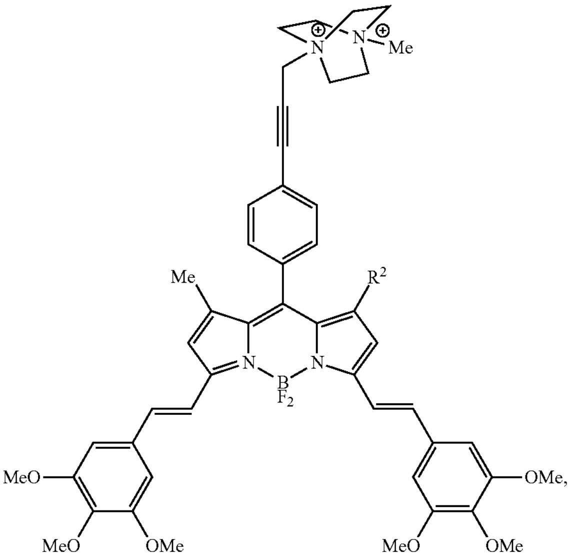
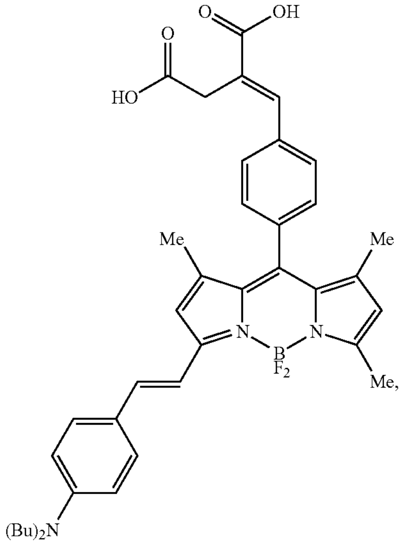

-continued
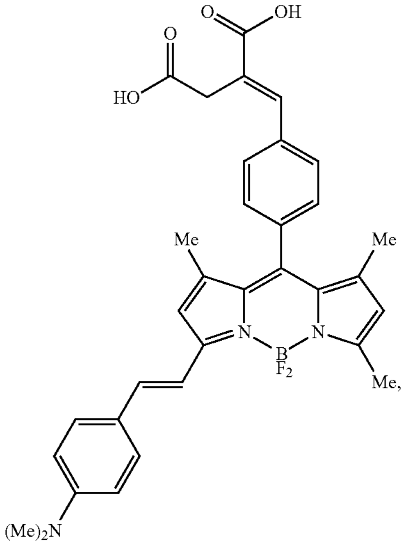
-continued
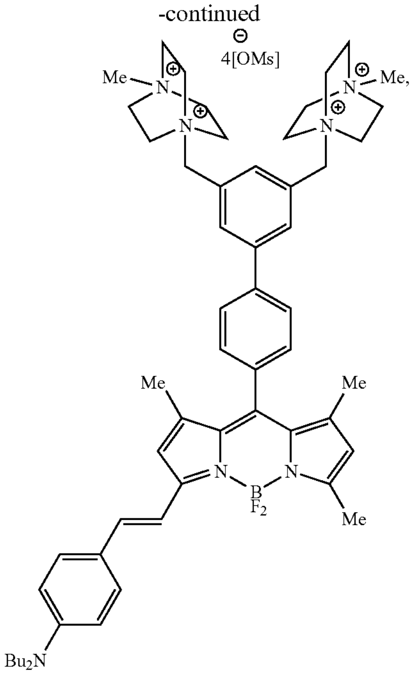
or a salt thereof. For instance, in some embodiments, the voltage sensitive dye is
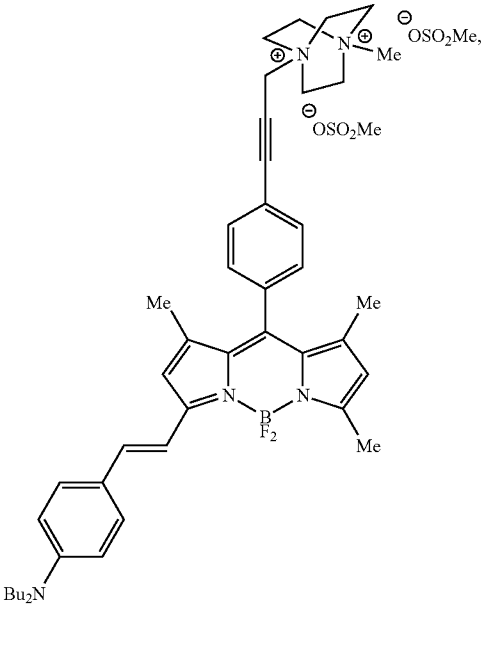
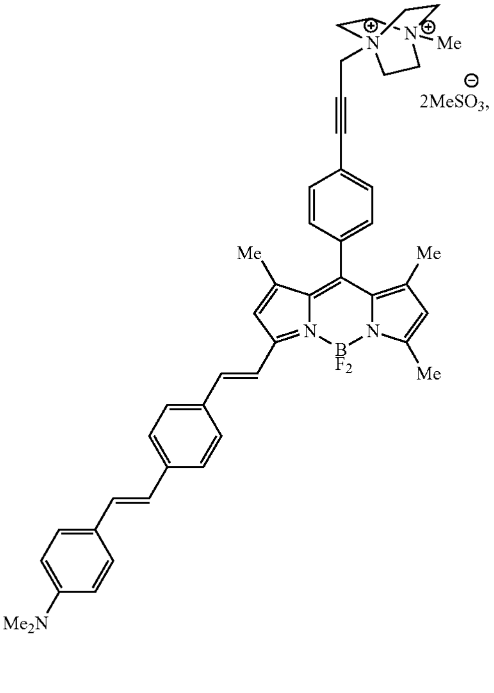

-continued
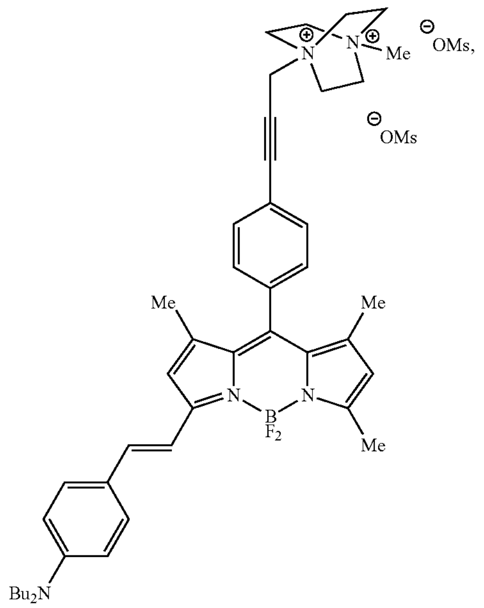
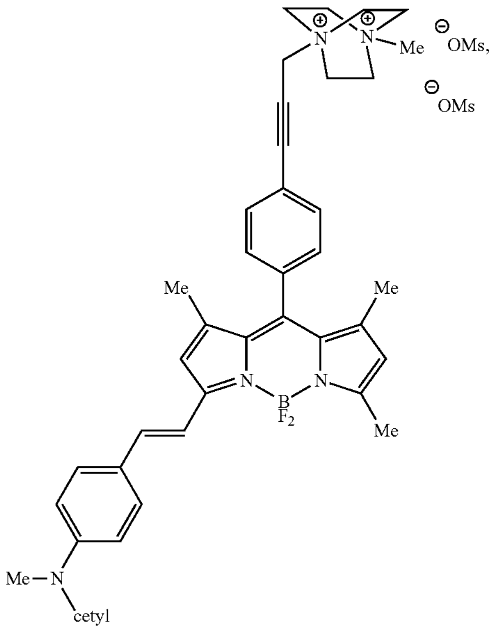
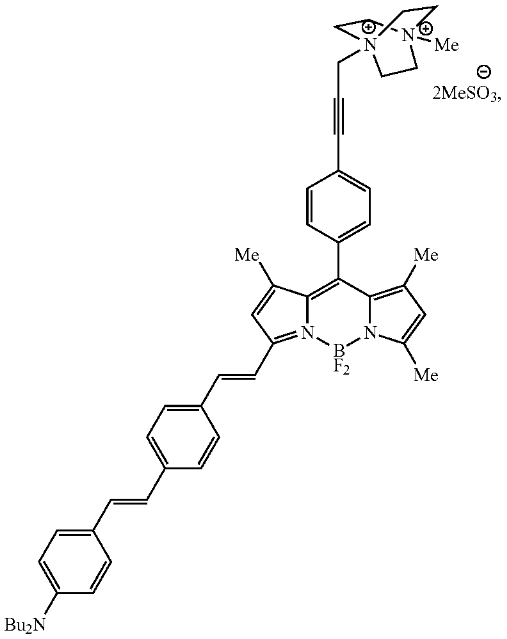
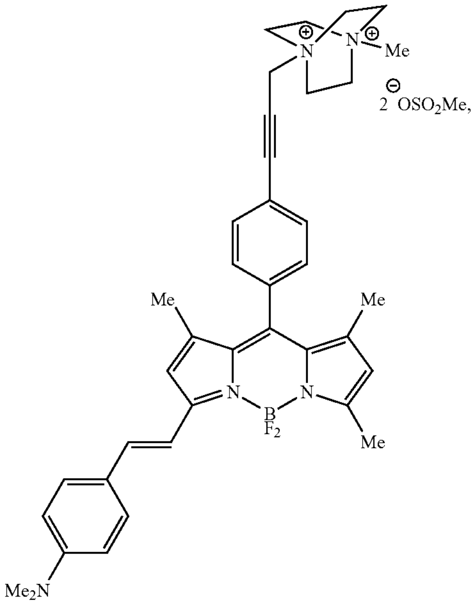

-continued
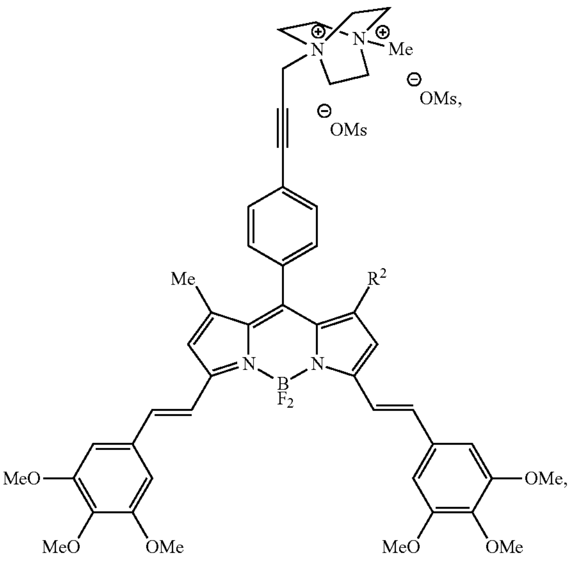
-continued
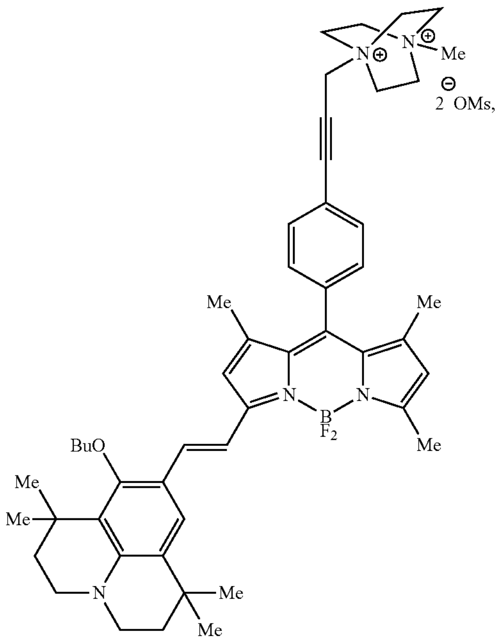
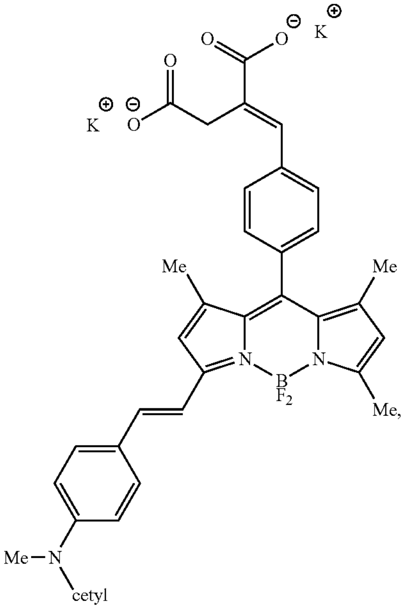
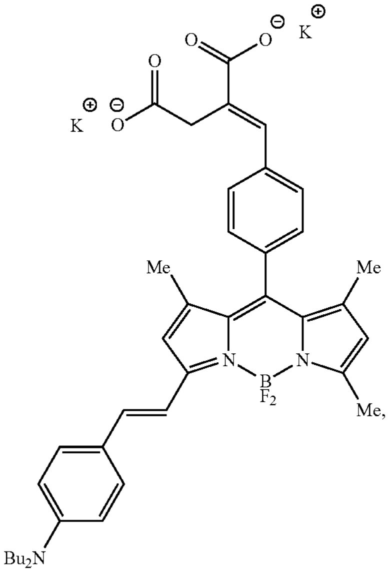
or

-continued

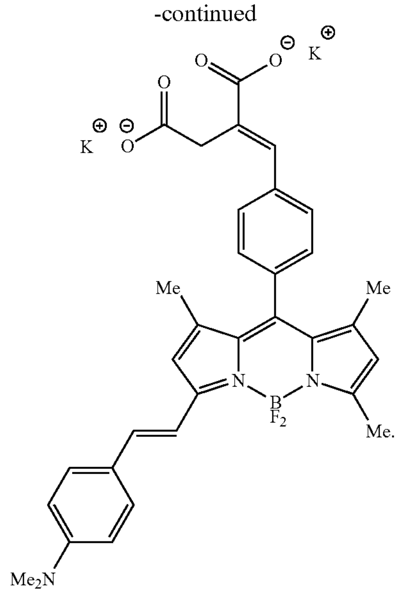

In some cases, the voltage sensitive dye is

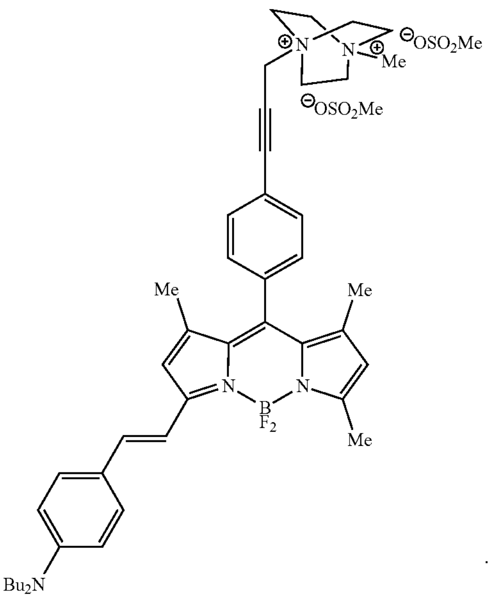

In certain embodiments, as exemplified in the chemical structures above, the voltage sensitive dye may comprise an optionally substituted condensed ring structure containing a boron atom, such as boron-dipyrromethene (BODIPY). Without wishing to be bound by theory, in certain aspects, the optionally substituted condensed ring structure containing a boron atom may confer the voltage sensitive dye with properties such as photostability. In certain embodiments, the optionally substituted condensed ring structure containing a boron atom may insert into the cell membrane.

In some embodiments, as exemplified in the chemical structures above, the voltage sensitive dye may comprise an electron donating group, such as dibutyl amine or an alkoxy group. Without wishing to be bound by theory, in some aspects, the electron donating group serves as a source of electrons and provides the molecule with voltage sensitivity.

In general, the substrate may be exposed to the dye using any suitable means. For example, the substrate may be immersed in the dye. As another example, a suitable amount of dye may be added to the surface of the substrate.

In general, any suitable substrate may be used. A suitable substrate may be configured to associate with cells. For instance, the surface of the substrate may comprise one or more functional groups that are capable of forming a non-covalent and/or covalent bond with moieties typically present on the cellular surface. In some embodiments, the substrate is a membrane. For instance, the substrate may be a nitrocellulose membrane.

In general, the method may be used with any suitable tissue sample and/or cells. In some embodiments, tissue sample and/or cell may originate from an animal. In some embodiments, the tissue sample and/or cell may originate from a human. In certain embodiments, the sample and/or cell may originate from plants, protists, and/or bacteria. In certain embodiments, the tissue sample and/or cell may originate from a biopsy. In other embodiments, the tissue sample and/or cell may originate from a cells grown in culture. In some embodiments, the cells and/or tissue may be non-excitable. In other instances, the cells and/or tissue may be excitable. In some embodiments, the cells and/or tissue may be non-embryonic. In other instances, the cells and/or tissue may be embryonic.

As noted above, the viability of the cells may be substantially maintained during the transfer process. For instance, the viability of the cells on the substrate may be greater than or equal to about 50%, greater than or equal to about 60%, greater than or equal to about 70%, greater than or equal to about 75%, greater than or equal to about 80%, greater than or equal to about 85%, greater than or equal to about 90%, greater than or equal to about 95%, greater than or equal to about 98%, or greater than or equal to about 99%. In some embodiments, the reduction in cell viability due to contacting cells with and/or transferring to the substrate may be less than or equal to about 30%, less than or equal to about 20%, less than or equal to about 15%, less than or equal to about 10%, less than or equal to about 5%, or less than or equal to about 2%.

Another aspect of the present disclosure relates to a kit for assessing membrane potential in cells. The kit may include a substrate configured to associate with cells and a voltage sensitive dye. In some embodiments, the kit may further comprise any solvents, solutions, buffer agents, acids, bases, salts, cell medium, etc. needed to maintain the viability of cells, dissolve the voltage sensitive dye, and/or analyze the cells. For instance, in some embodiments, the kit may include a control dye. The control dye may serve to facilitate calibration of the dye, calculation of dye concentration, modulate one or more features of the voltage sensitive dye (e.g., charge state). Different kits may be available for different voltage sensitive dyes. The kit may also include instructions on how to use the materials in the kit. The kit may also include image analysis software and/or access to an image analysis software.

Another aspect of the present disclosure relates to a system for assessing membrane potential in cells. In some embodiments, the system comprises a layer comprising living cells on a membrane (e.g., nitrocellulose) and a voltage sensitive dye associated with at least a portion of the living cells. The properties of the cells, membrane, and/or voltage dye may be as described herein. For instance, the living cells may be non-covalently bound to the membrane. In certain embodiments, the layer may comprise extracellular matrix.

As used herein, the term "animal" refers to any member of the animal kingdom. In some embodiments, "animal" refers to a human, at any stage of development. In some embodiments, "animal" refers to a non-human animal, at any stage of development. In some embodiments, animals include, but are not limited to, mammals, birds, reptiles, amphibians, fish, and/or worms. In certain embodiments, the non-human animal is a mammal (e.g., a rodent, a mouse, a rat, a rabbit, a monkey, a dog, a cat, a sheep, cattle, a primate, and/or a pig). In some embodiments, an animal may be a transgenic animal, genetically-engineered animal, and/or clone.

As used herein, the phrases "associated with" or "form associations" has its ordinary meaning in the art and may refer to when two entities are linked by a direct or indirect covalent or non-covalent interaction. Preferably, the association is covalent. Desirable non covalent interactions include hydrogen bonding, van der Waals interactions, hydrophobic interactions, magnetic interactions, electrostatic interactions, etc.

As used herein, the term "charged group" has its ordinary meaning in the art and may refer to a group comprising one or more charged moiety. As used herein, a "charged moiety" is a chemical moiety that carries a formal electronic charge, e.g., monovalent (+1), divalent (+2), trivalent (+3), etc. The charged moiety may be anionic (i.e., negatively charged) or cationic (i.e., positively charged). Examples of negatively-charged groups or precursors thereof, include carboxylate groups, sulfonate group, sulfate groups, phosphonate groups, phosphate groups, hydroxyl groups, and the like. Examples of positively-charged moieties include amino groups (e.g., protonated primary, secondary, and/or tertiary nitrogen atoms), quaternary ammonium groups, quaternary phosphonium groups, pyridinium group, and imidizolium groups. In a particular embodiment, the charged moieties comprise quaternary ammonium groups and/or quaternary phosphonium groups. In some cases, one or more charged moieties are positively charged. In certain embodiments, all of the charged moieties are positively charged. Without wishing to be bound by theory, the charge of the charged moiety may vary, in some cases, with the environmental conditions, for example, changes in pH may alter the charge of the moiety, and/or cause the moiety to become charged or uncharged. In certain aspects, for example, one or more charged moieties may be positively charged, negatively charged, or neutral, depending on the environmental conditions (e.g., pH). In certain non-limiting embodiments, as exemplified by the structures herein, the voltage sensitive dye may comprise one or more carboxylic acid groups. In some such embodiments, at physiological pH, the one or more carboxylic acid groups may dissociate, therefore yielding one or more negatively-charged carboxylate salts, depending on the counterions present. For example, in some aspects, one or more voltage sensitive dyes that are provided in a carboxylic acid form dissociate when exposed to tissue, cells, or a cell culture, such that the dye becomes negatively charged and comprises one or more carboxylate salts. In some non-limiting embodiments, the one or more voltage sensitive dyes may comprise one or more charged (e.g., negatively charged) carboxylate salts, as exemplified by the structures herein, when exposed to tissue, cells, or a cell culture. Typically, the charge of a moiety is determined under environmental conditions at which the dye is used. In general, the charge density of the dye may be selected as desired. In some embodiments, the charged moiety is not a metal (e.g., copper).

Typically associated with the charged moiety are one or more counterions, such that the charged moiety and the counterions together are electroneutral (i.e., have a zero net electronic charge). Thus, positively charged moieties may be associated with an anionic charged moieties (e.g., anionic counterion), while negatively charged moieties (for example, carboxylates, sulfonates, etc.) may be associated with a cationic charged moieties (e.g., cationic counterion). The counterion may be any suitably charged moiety, atomic or molecular, that can associate with the charged moiety of the dye. The counterions can be loosely associated with the charged moiety in some instances, i.e., the counterions can be exchanged under ambient conditions with the same or different ions (e.g., $Li^+$ may be exchangeable for $Li^+$ or $Na^+$, etc.).

A cationic counterion may be associated with a negatively charged moiety. For example, if the charged moiety has a −1 charge, the counterions may be any ions having a +1 charge, for example, alkali metals such as $Na^+$, $Li^+$, $K^+$, etc., and/or other +1 charged species, such as $Cu^+$, $NH_4^+$, etc. Similarly, if the charged moiety has a −2 charge, the counterions may be any ions having a +2 charge, for example $Ca^{2+}$, $Be^{2+}$, $Fe^{2+}$, $Mg^{2+}$, $Cu^{2+}$, $Ni^{2+}$, $Sn^{2+}$, $Zn^{2+}$, $2Na^+$, $2Li^+$, $2K^+$, $Li^+$ and $Na^+$, $Li^+$ and $K^+$, $Na^+$ and $K^+$, etc. More than one counterion may be present in some cases.

An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$

, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, and the like), $BF_4^-$, $PF_4^-$, $PF_6^-$

, $SbF_6^-$, $B[3,5-(CF_3)_2C_6H_3]_4]^-$, $BPh_4^-$,

A $Al(OC(CF_3)_3)_4^-$, and a carborane anion (e.g., $CB_{11}H_{12}^-$ or $(HCB_{11}Me_5Br_6)^-$).

As used herein, the term "pharmaceutically active agent" refers collectively to biomolecules, small molecules, and bioactive agents which exert or induce a biological effect upon administration to an animal.

As used herein, the term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "subject" refers to any mammal, including a human, or non-human subject. Non-human subjects can include experimental, test, agricultural, entertainment or companion animals. A subject may be a human. A subject may be a domesticated animal, such as a dog, cat, cow, goat, sheep, pig, etc. A subject may be an experimental animal, such as a mouse, rat, rabbit, monkey, etc.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

The following examples are intended to illustrate certain embodiments of the present invention, but do not exemplify the full scope of the invention.

Example 1

This examples describes an exemplary voltage membrane imaging method for assessing cell membrane potential. The method can be used by pathologists to quickly gather important information about cells excised during biopsies.

Figure 2:
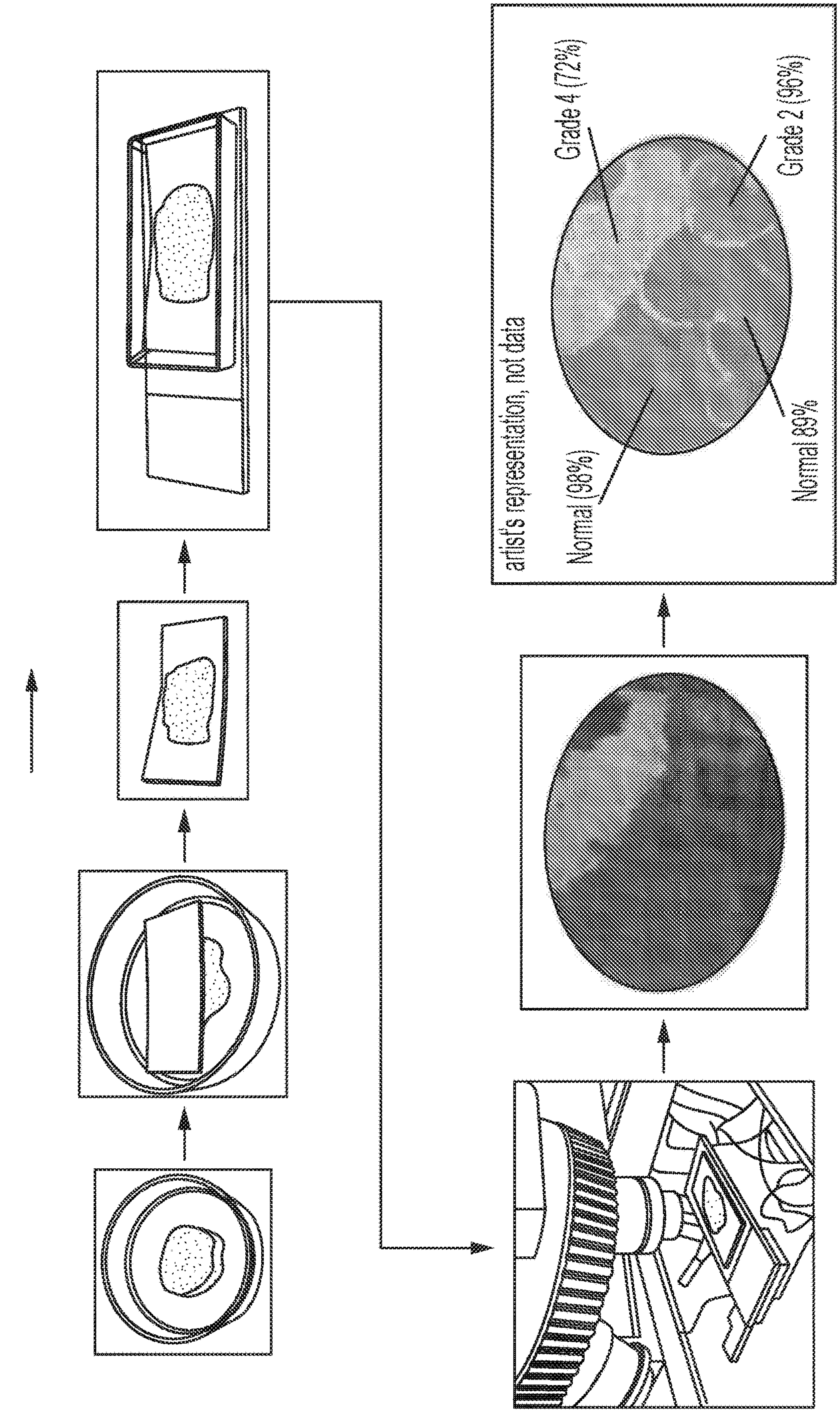
FIG. 2 shows an exemplary method, according to one set of embodiments.

FIG. 2 shows an exemplary voltage membrane imaging method. First, a precut nitrocellulose (NC) strip is gently placed onto a tissue section. Then, the precut nitrocellulose strip is lifted off. NC is extremely sticky to cells, thus a thin, mirror-image layer of living cells is lifted from the section; the section is then sent for standard pathology or biomarker study. The attached cells to the strip ("print") stay alive for many hours if kept in the appropriate cell-culture medium. The print was immediately immersed in a voltage sensitive dye suspended in culture medium in the chamber well slide. The voltage sensitive dye had the following structure:

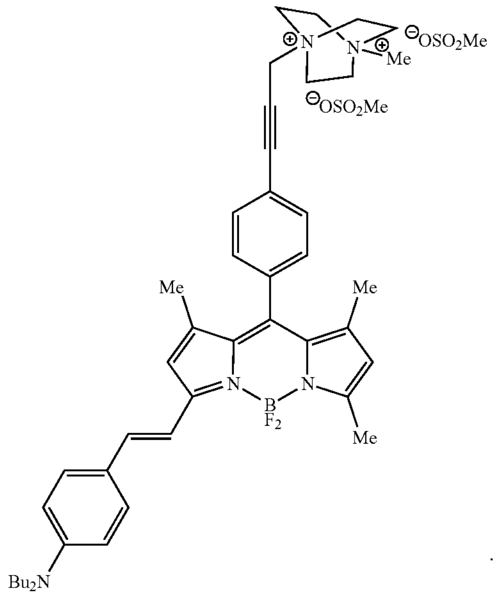

The print stays in the dye for 15 minutes then they dye is poured off, and the dye is washed off by filling the chamber with plain culture medium, which is then poured off. A few drops of culture medium are put onto the print, then the chamber well is removed and the print is covered with a coverslip. The print is then ready to be scanned by eye and/or photographed with a microscope and a Cy5 fluorescence filter set (e.g., Semrock Cy5-4040A), and equipped with a slide scanner. The intensity of the fluorescent signal is the readout of the plasma membrane resting potential (Vmem) of the living cells. Multiple images will need to be created in order to image the entire tissue print; this can be accomplished by rastering across the sample by hand or using an automated a slide scanner, then employing commonly available stitching software to assemble one single, patchwork of the entire tissue print. That image of the Vmem magnitude and pattern is then uploaded to our web-based image analysis software, which returns the analysis in seconds as illustrated in FIG. 2.

The analysis will include a map delineating the boundaries of cells and cell groups that have been distinguished by their differing membrane voltage patterns. The software also predicts the metastatic potential of the groups (i.e. normal, moderate potential, high potential, or using the schema that is used for a particular cancer type, such as the Grade 1, 2, and 3 system used for breast cancer). The prediction is accompanied by a measure of the confidence with which the program made the map and assigned the interpretations. This can then be downloaded and provided to the surgeon in well under an hour, with time ultimately being proportional to the size of the sample. Thus, the pathologist will have a preliminary map of the predicted location of suspect cells, and the surgeon will have unbiased data about what has been removed to use when deciding if the surgery has been successful.

Example 2

This examples describes the use voltage membrane patterns to distinguish between the metastatic potential of cells.

Human cancers are heterogeneous at multiple levels, as can be demonstrated by histology, DNA alterations and malignant patterns of gene expression. Solid tumors, including breast and prostate cancers, can be classified histologically as low-grade (indolent) or high-grade (more aggressive) malignancies. It's the pathologist's task to evaluate surgical resection and biopsy specimens in order to identify the areas suspicious for cancer that need to be processed for histological examination, but relatively few technologies are available to support this labor-intensive process. It is known that the alterations in tissue structure, which is used to recognize invasive cancer and predict its clinical behavior, are associated with changes in cell physiology, but such changes can be difficult to measure in human specimens. The method in this example leverages advance in imaging technologies as a platform for rapid identification of cancer in human surgical and biopsy specimens. These innovative imaging technologies allow the resting membrane voltage (Vmem) to be visualized in living cells by using Voltage Sensitive Dyes (VSDs). Normal cells and tissues maintain stereotypical patterns of Vmem; these patterns are recognizable in Vmem Imaging as bioelectric signatures. Membrane voltage, or resting potential (Vmem), regulates behaviors that are disrupted in cancer, including proliferation, migration, apoptosis, homeostasis, and cell-cell signaling.

The print system in combination with Vmem imaging can be used to detect important differences in malignant potential by visualizing otherwise invisible functional phenotypes. Breast cancer cell lines that have diverged as sublines that have different metastatic potential show different membrane voltage patterns that are clearly distinguishable by Vmem Imaging, especially when combined with computer aided image analysis techniques as illustrated in FIG. 3. The methods, described herein, represent an important new approach to visualizing functional cancer phenotypes both in cancer models and as they present in human tumors.

Vmem Imaging is a relatively new technique that reveals essential, and until now invisible, information about the behavior and physiology of large populations of cells, including degree of differentiation and cell fate. Vmem imaging yields information about live cell physiology that is directly relevant to studies and evaluation of cancer. All of this valuable data is lost in frozen and fixed preparations, thus Vmem imaging has the potential to significantly improve our understanding of cancer and its malignant potential. The VSDs, described herein, make it possible to image many cells simultaneously and for long periods of time.

Vmem imaging relies on live cell imaging using VSDs. It is the brightness of their fluorescence, usually shown as color differences, that is a readout of the Vmem. The differences between dye types arise from differences in how the Vmem affects the brightness. It has been known for some time that most cancer cells are depolarized (the Vmem is less negative) relative to their normal counterparts; indeed some of the pumps and channels that contribute to establishing Vmem are being studied as cancer drug targets. Classic electrophysiology using electrodes can only measure membrane potential in one cell at a time and yields a single measurement. In contrast, using VSDs allow stereotyped patterns of Vmem to be captured. The discovery of these patterns was unexpected and previously unknown. These patterns, sometimes referred to as signatures, vary with malignant potential. Thus, Vmem Imaging may be used to identify malignant cells in a field of normal cells. Because a pattern intrinsically contains more information than a single measurement, Vmem Imaging data provide more information to use for interpretation of cell phenotype. Moreover, Vmem patterns in non-excitable cells and tissues reflect physiological processes of keen interest in drug development and other translational research.

Figure 3A:
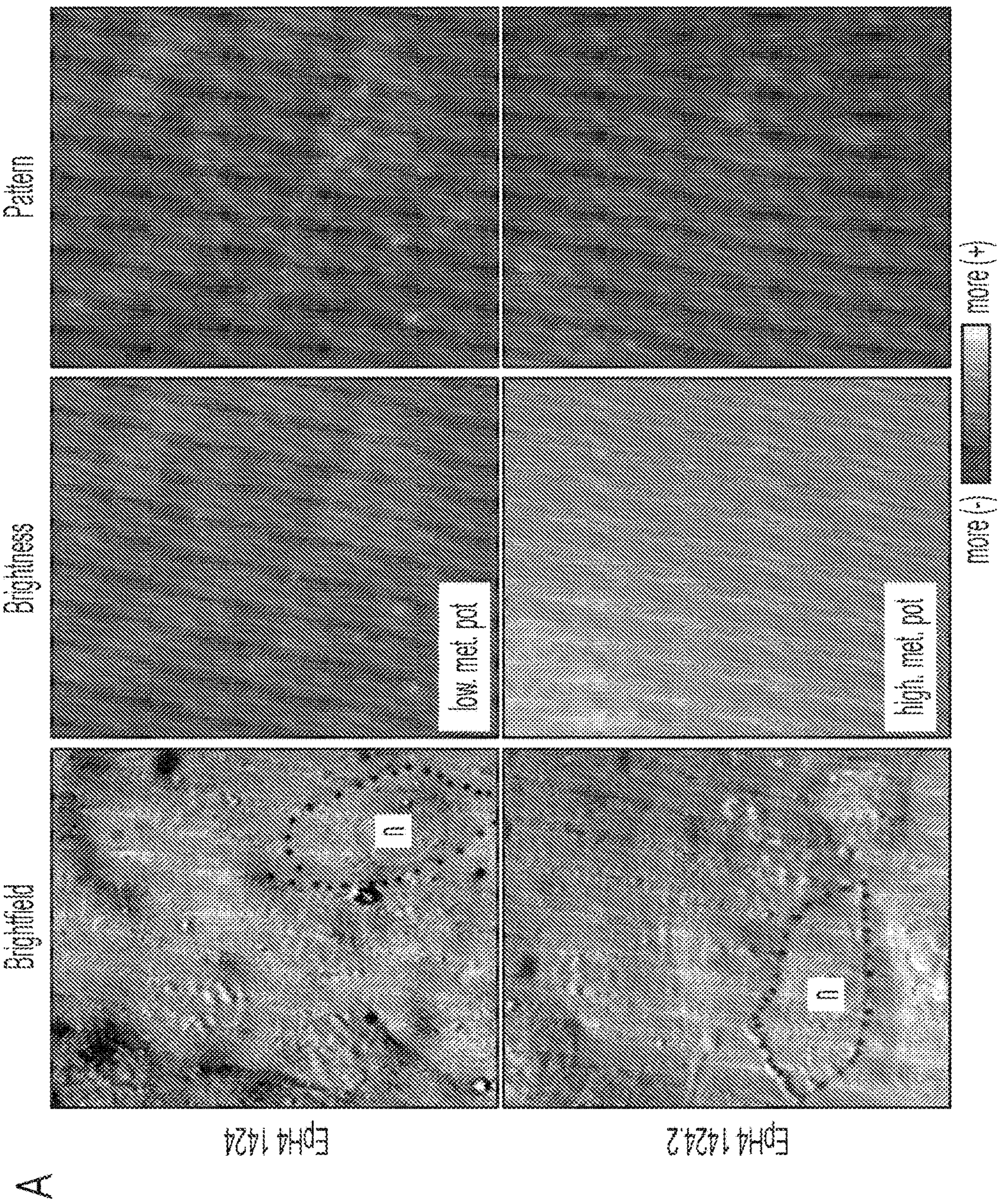
FIGS. 3A-B show (A) images of cells that differ in metastatic potential and (B) a plot of pattern versus mean brightness, according to one set of embodiments.
Figure 3B:
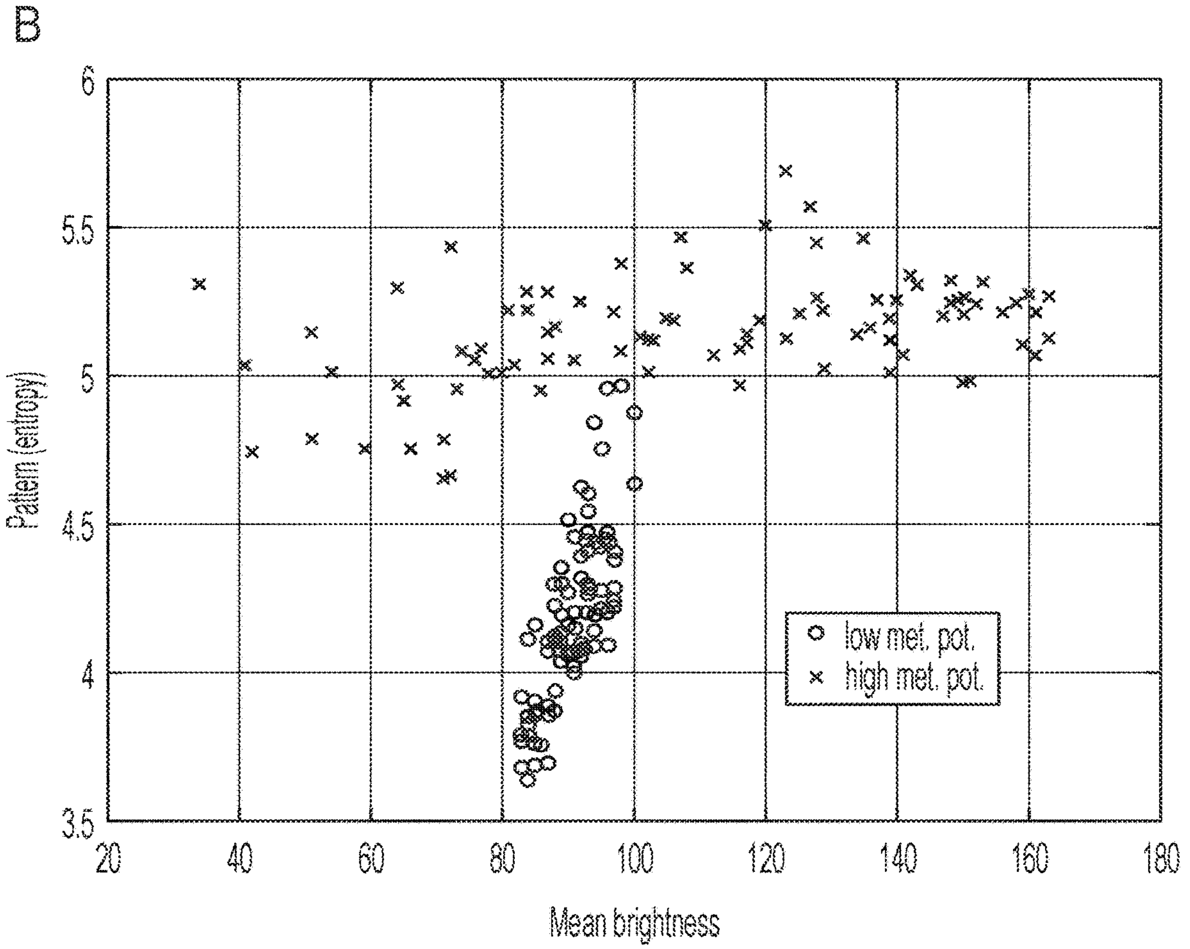

FIG. 3 shows Vmem imaging of mouse breast cancer cell lines EpH4 1424 (low metastatic potential) and EpH4 1424.2 (sister clone derived from a lung metastasis), plus automated analysis. Sister ATCC cell lines representing mouse breast cancers that differ in metastatic potential were grown in standard 2-D cultures and imaged using the CC2-DiBAC Vmem imaging dyes. FIG. 3A shows bright field and un-manipulated Vmem images (left and middle columns) of these two live cancer cell lines grown in standard 2-D culture. One cell of each type has been outlined and its nucleus indicated with an "n". In the Vmem images, different colors represent different Vmems. The brightness of the images in the third column has been manipulated to show the pattern of different Vmems. The difference in the average value of brightness/Vmem is clear by visual inspection. The cultures show no difference in bright field, but the Vmem phenotypes are obviously different. To analyze these Vmem images, each image was tiled into 128×128 pixel regions and computed two image metrics for each. FIG. 3B shows output from computer analysis of the images. Specifically, FIG. 3B shows a scatterplot of those features—entropy (a measure of information in the pattern) and mean intensity (value)—color-coded by cell type. While difficult to distinguish with the naked eye, pattern differences are rapidly detected and quantified using computer-aided analysis techniques, such as quantification of information content by the parameter entropy, which relates to the complexity of the pattern. This quantification shows something novel—the cells with higher metastatic potential are not less negative, their charge varies more, consistent with evidence for reduced gap junctional communication among these cells. The opposite is true of the cells derived from tumors of low metastatic potential that vary less in charge. Cells from the line with higher metastatic potential also have both higher overall entropy and greater variation across the culture. In addition, the Vmem of cells with lower metastatic potential shows much more tightly clustered intensity values, with overall and mean lower entropy. The quantification findings were surprising and unexpected.

Example 3

This example describes a comparison between standard histopathological staining techniques and the voltage membrane imaging method described in Example 1 for a prostate tissue sample.

Figure 4:
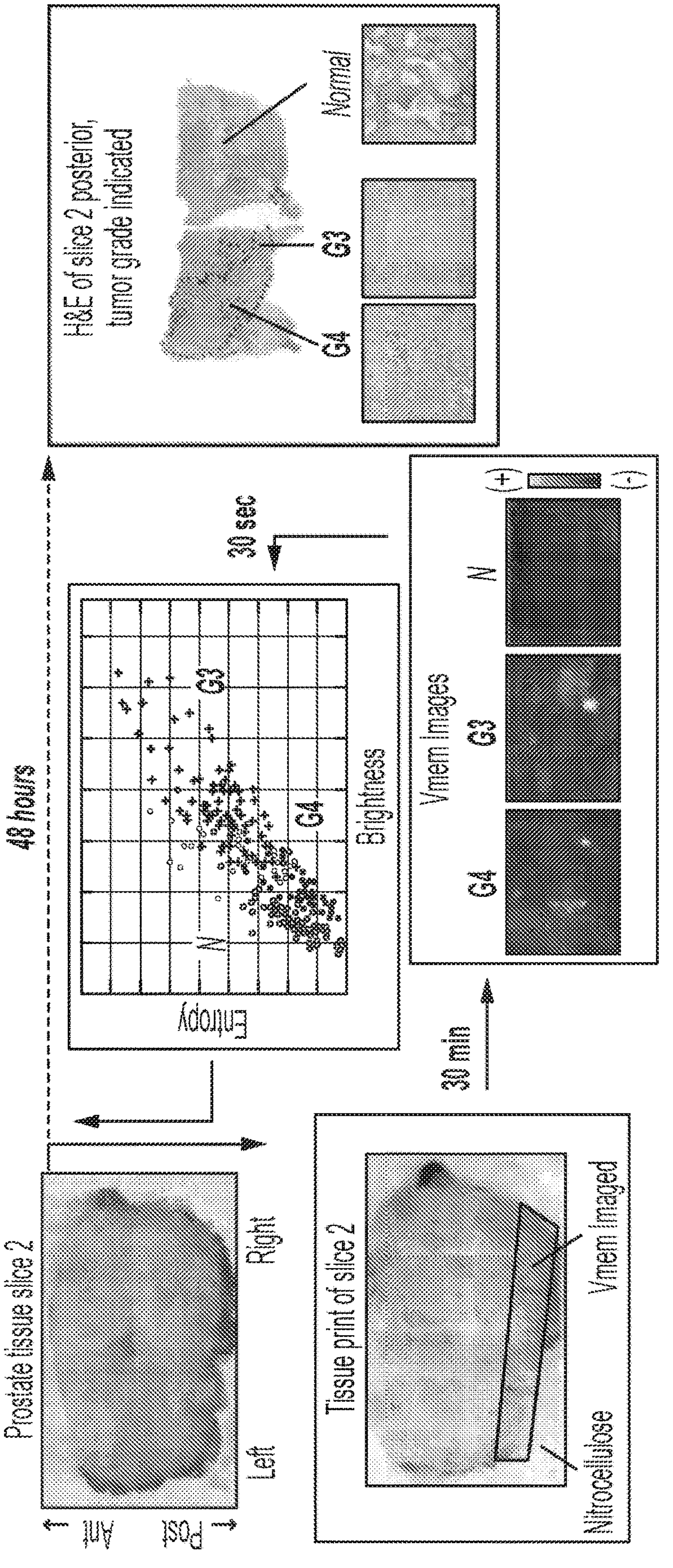
FIG. 4 shows an exemplary method using a prostate tissue sample, according to one set of embodiments.

FIG. 4 shows the comparison between the two methods. Blue arrows indicate the standard processing of the prostate specimens. This prostate was excised then sliced into sections by the pathologist. All tissue slices were submitted for pathology review as usual. The result of that pathology review of tissue slice 2 is illustrated in the right panel, available between 48 hours and 10 days after surgery. The top image in the right panel shows a picture of the slide with hematoxylin and eosin (H&E) staining of the posterior half of Slice 2, with regions of differing tumor grade demarcated by the pathologist (i.e., G3: Low Grade Cancer, Gleason pattern 3; G4: High Grade Cancer, Gleason pattern 4, N: Normal prostate tissue). The bottom right panel shows three 10× images. The other panels illustrate Vmem imaging techniques. Red arrows indicate the sequence. A print was made of the fresh prostate slice, as in Example 1, and orientation markers were added to both tissue and nitrocellulose. Regions from the boxed area indicated on the print were slide mounted and treated with a drop of dilute voltage sensitive dye of Example 1. Vmem Imaging began about 15 minutes later. Vmem Images from the areas of interest indicated by the histology were analyzed for brightness and entropy.

Example 4

This is a prophetic example that describes the use of the voltage membrane imaging method on cells grown in culture. This method is valuable for comparing the effect of pharmaceutically active agents on in vitro model systems with the results of in vivo tests, to ascertain the applicability of in vitro tests.

In this example, rather than applying the substrate to a piece of tissue, the membrane is applied to the cells growing in a culture dish. The membrane would then be treated as in the other examples, that is, the cells would be exposed to the dye, and the fluorescent signal would be recorded using a camera attached to a fluorescence microscope, then analyzed by eye or by software.

Example 5

This is a prophetic example that describes the use of the voltage imaging method on cells from living cells outside of the animal kingdom, including plants, fungi, protozoans, and bacteria. The substrate is applied to a sectioned plant stem or root, or a microbial mat/bacterial film. This is valuable for examining the effects of antimicrobials or antibiotics as well as for ascertaining the bioelectric characteristics of these cells to better understand their biology. The membrane would then be treated as in the other examples, that is, the cells would be exposed to the dye, and the fluorescent signal would be recorded using a camera attached to a fluorescence microscope, then analyzed by eye or by software.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

We claim:

1. A method for controlling a treatment of a subject by determining a metastatic potential of cells and/or an extent of a potential pathological disorder in a tissue from the subject, the method comprising the steps of:

(1) contacting a surface of a tissue from the subject with a substrate for a sufficient period of time, wherein the surface of the tissue comprises cells and/or extracellular matrix, and wherein the sufficient period of time allows for a binding comprising associations, non-covalent bonds, and/or covalent bonds to form between the substrate and the cells and/or extracellular matrix, whereby allowing at least a portion of the cells and/or extracellular matrix to bind to the substrate;

transferring the at least a portion of the cells from the surface of the tissue to the substrate via the binding to the substrate, wherein a cell viability of the at least a portion of the cells after the transferring step is greater than or equal to about 75% to provide living cells thereon and removing the substrate from the surface of the tissue, (2) exposing the cells and/or extracellular matrix on the substrate to a voltage sensitive dye (VSD), obtaining a $1^{st}$ visualization of a resting membrane voltage (Vmem) in a whole layer of cells and/or extracellular matrix on the substrate using a microscope with the VSD, obtaining as a $2^{nd}$ visualization by visualizing a resting membrane voltage (Vmem) in only the living cells on the substrate with the VSD, and using a computer with software to combine the $1^{st}$ and $2^{nd}$ visualizations with a computer aided image analysis that includes a dividing up of both the visualizations each into a plurality of regions for each the $1^{st}$ visualization and the $2^{nd}$ visualization, to produce a comparison of a pattern entropy or a measure of an information versus a mean intensity for each cell type, whereby cells from a tumor with a higher metastatic potential have both higher overall entropy and greater variation across $1^{st}$ visualization;

(3) using the computer with software to compare a mean intensity and/or brightness to a variance of Vmem, to obtain a measurement of variance of Vmem including a largest variance and a lowest variance, for each region from each of the plurality of regions;

whereby regions that have a largest variance of Vmem contain a highest metastatic potential of cells and/or a highest amount of abnormal cells, and regions that have a lowest variance of Vmem contain a lowest metastatic potential of cells and/or a lowest amount of abnormal cells; whereby cells that are derived from a tumor with a higher metastatic potential include a charge that varies more, whereby cells that are derived from a tumor of low metastatic potential vary less in charge; and (4) executing a diagnosis and/or a pathological assessment on the tissue of the subject based upon the largest variance and the lowest variance in step (3) and the cells that have the higher metastatic potential and the cells that have the lowest metastatic potential, and controlling a treatment of the subject using the diagnosis and/or the pathological assessment.

2. The method of claim 1, wherein the at least a portion of the cells form a layer on the substrate, wherein the layer has a shape having a perimeter and the perimeter is within about 20% of a perimeter of the surface of the tissue.

3. The method of claim 2, wherein an area of the layer is within about 20% of an area of the surface of the tissue.

4. The method of claim 1, wherein the surface of the tissue comprises a first cell and a second cell that are separated by a first distance, wherein the first cell and the second cell are transferred to the substrate, and wherein a second distance between the first cell and the second cell on the substrate is within about 20% of the first distance.

5. The method of claim 1, wherein the at least a portion of the cells comprises at least about 70% of the cells on the surface of the tissue.

6. The method of claim 1, further comprising exposing the at least a portion of the cells on the substrate to a fluorescent voltage sensitive dye configured to provide a change in fluorescence in a response to a different voltage.

7. The method of claim 1, wherein the at least a portion of the cells comprise cancer cells.

8. The method of claim 1, wherein the at least a portion of the cells comprise one or more cells having an abnormality.

9. The method of claim 1, further comprising obtaining a two-dimensional fluorescence image of the at least a portion of the cells on the substrate and determining a fluorescence intensity of one or more cells on the substrate based at least in part on the two-dimensional fluorescence image.

10. The method of claim 9, further comprising determining a variance and/or pattern in the fluorescence intensity across at least a portion of the substrate based at least in part on the two-dimensional fluorescence image.

11. The method of claim 9, further comprising determining whether the subject has a pathological disorder based at least in part on the two-dimensional fluorescence image.

12. The method of claim 1, wherein the sufficient period of time is in a range from 1-60 seconds.

13. The method of claim 1, further comprising contacting the cells on the substrate with a culture medium configured to keep cells alive before and/or during a visualization.

14. The method of claim 1, further comprising the computer with software are accessed by an uploading of a visualization to a web-based image analysis software which is configured to return an image analysis.

* * * * *